(12) United States Patent
Huang et al.

(10) Patent No.: US 6,514,229 B1
(45) Date of Patent: *Feb. 4, 2003

(54) SAFETY SYRINGE WITH A NEEDLE SLEEVE

(75) Inventors: Wu-Shun Huang, Taipei (TW); Chung-Jen Lee, Taipei (TW)

(73) Assignee: Formosa Medical Devices Inc., Taipei (TW)

(*) Notice: Subject to any disclaimer, the term of this patent is extended or adjusted under 35 U.S.C. 154(b) by 131 days.

This patent is subject to a terminal disclaimer.

(21) Appl. No.: 09/588,322

(22) Filed: Jun. 6, 2000

(51) Int. Cl.[7] .................................................. A61M 5/32
(52) U.S. Cl. ....................... 604/198; 128/919; 604/110; 604/263
(58) Field of Search ................................. 604/110, 163, 604/181, 187, 188, 192, 195, 197, 198, 218, 228, 235, 239–243, 263, 264; 128/919

(56) References Cited

U.S. PATENT DOCUMENTS

| | | | | |
|---|---|---|---|---|
| 3,703,174 A | * | 11/1972 | Smith ......................... 221/278 |
| 4,897,083 A | * | 1/1990 | Martell. ....................... 604/192 |
| 4,898,589 A | * | 2/1990 | Dolgin et al. ................ 604/110 |
| 5,047,016 A | * | 9/1991 | Dolgin et al. ................ 604/110 |
| 5,195,985 A | * | 3/1993 | Hall ............................ 604/110 |
| 5,344,404 A | * | 9/1994 | Benson ........................ 604/110 |
| 5,366,447 A | * | 11/1994 | Gurley ........................ 604/192 |
| 5,569,203 A | * | 10/1996 | Chen ........................... 604/110 |
| 5,741,236 A | * | 4/1998 | Kakiuti ........................ 604/192 |
| 5,899,887 A | * | 5/1999 | Liu .............................. 604/110 |
| 6,033,385 A | * | 3/2000 | Liu .............................. 604/110 |

* cited by examiner

*Primary Examiner*—Anhtuan T. Nguyen
*Assistant Examiner*—Michael M. Thompson
(74) *Attorney, Agent, or Firm*—Rosenberg, Klein & Lee

(57) ABSTRACT

A safety syringe with a needle sleeve is provided. The needle sleeve is put around a cap of the syringe with a shoulder portion inside the needle sleeve abutting against a rear flange of the cap, such that the cap, a hub tightly fitted in the cap, and the needle sleeve together form a needle sleeve assembly, which allows the hub to temporarily locate closely before a neck portion of a barrel of the syringe, so that the syringe may be sterilized under high temperature without stress deformation and thermal deformation. When the cap is depressed, the hub and a cannula held thereto are caused to move backward and be stably retained to the neck portion of the barrel in an airtight relation. And when the cap is pulled forward again, it brings the needle sleeve to together separate from the hub to expose the cannula for injection.

4 Claims, 7 Drawing Sheets

SAFETY SYRINGE WITH A NEEDLE SLEEVE

BACKGROUND OF THE INVENTION

There are many safety syringes developed particularly to prevent discarded syringes and/or cannulas from unexpectedly stabbing and therefore undesirably injuring and infecting other people, including nursing and cleaning persons. U.S. Pat. Nos. 5,562,627; 5,405,327; 5,569,203; 5,899,887; 5,395,346, etc., all disclose syringes having specially associated hubs and barrels, so that hubs and cannulas held thereto of used syringes can be pulled back into the barrels without the risk of unexpectedly stabbing other people.

However, all these safety syringes of prior art developed to improve conventional syringes have a common problem. That is, although the hubs of these safety syringes may be stably connected to the barrels and be pulled back into the latter after the syringes have been used, the hubs are not always connected to the barrels in an airtight relation. As it is well-known that, when such safety syringes are assembled in the manufacturing process thereof, the hubs and the barrels must first be associated with one another before the syringes are sterilized, so that the assembled syringes would not be contaminated after the sterilization due to contact of any part of the syringes. However, the assembled hubs and barrels are subject to stress deformation and thermal deformation during the sterilization under high temperature and such deformation would have adverse influence on the stable and airtight connection of the hubs to the barrels.

It is therefore tried by the inventor to develop a further improved safety syringe to eliminate the drawbacks existing in the safety syringes of prior art.

SUMMARY OF THE INVENTION

A primary object of the present invention is to provide a safety syringe with a needle sleeve that is particularly made to improve a conventional safety syringe with a retractable hub. The needle sleeve of the safety syringe of the present invention allows the syringe to be sterilized with the hub and the barrel thereof in a contacted but non-engaged state, so that no stress deformation of the syringe would occur to adversely affect the airtight connection of the hub to the barrel of the syringe after the sterilization.

Another object of the present invention is to provide a safety syringe with a needle sleeve, so that the needle sleeve firmly holds the cap, the hub, and the barrel together to, on the one hand, prevent the cannula connected to the hub and covered by the cap from contamination by externally contacting the cannula, and, on the other hand, enable easy assembling of the hub to the barrel of the safety syringe simply by depressing the cap. And, the cap can be then pulled forward again to bring the needle sleeve to together separate from the syringe to expose the cannula for injection.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
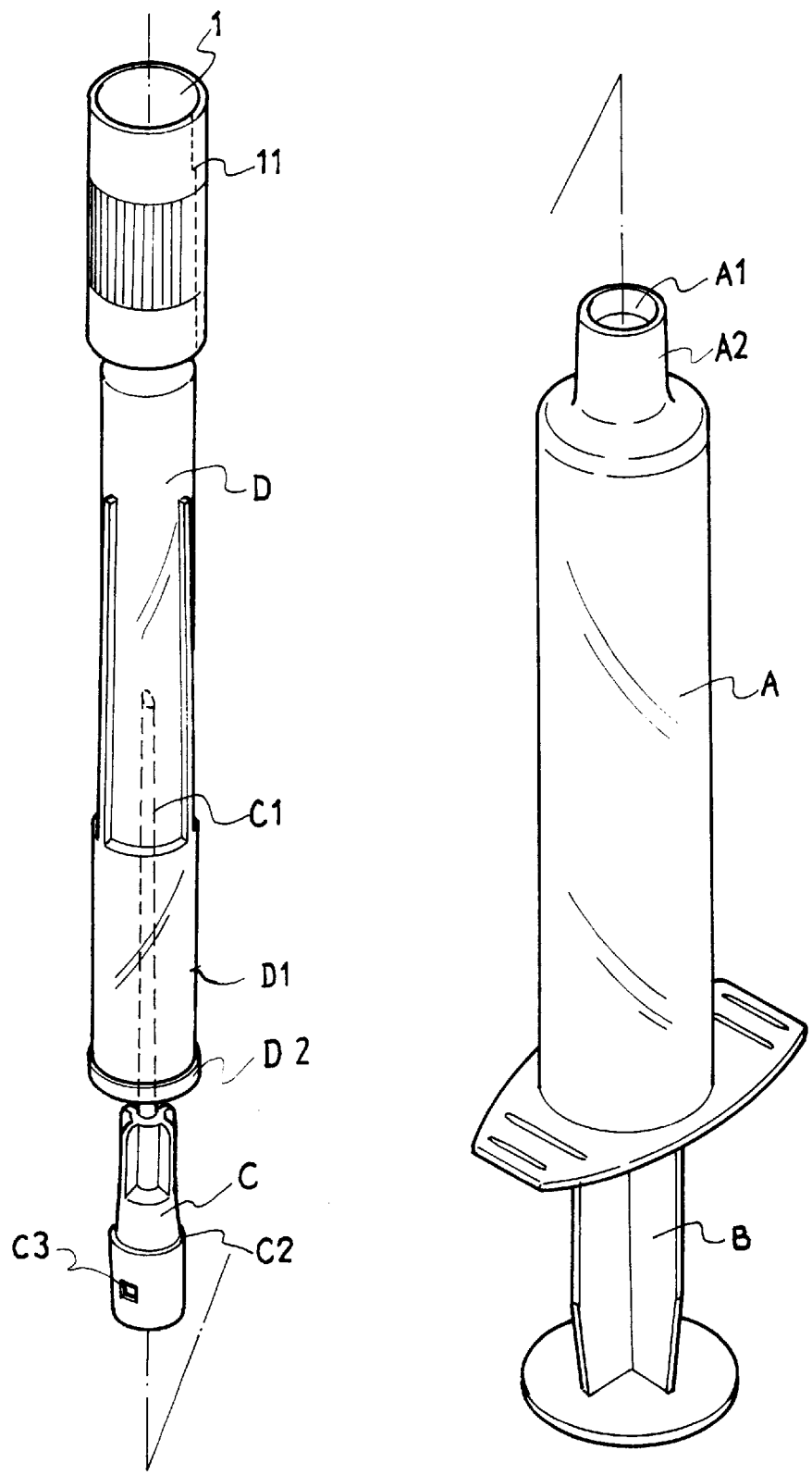
FIG. 1 is an exploded perspective of a safety syringe with a needle sleeve according to the present invention.

Please refer to FIG. 1 that is an exploded perspective of a safety syringe with a needle sleeve according to the present invention. The safety syringe mainly includes a barrel A, a plunger B slidably mounted in the barrel A, a hub C connected to a front end of the barrel A for holding cannula C1 thereto, and a cap D for covering the cannula C1, and is characterized in a needle sleeve 1 put around joints of the hub and the barrel and of the hub and the cap, as can be best seen in FIG. 3.

Figure 2:
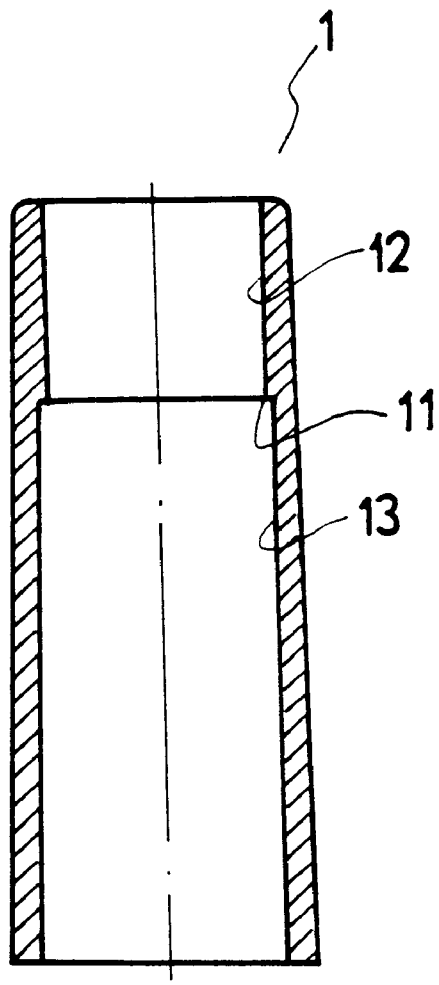
FIG. 2 is a sectional view of the needle sleeve of the present invention.

Please refer to FIG. 2. The needle sleeve 1 is a hollow tube defining an inner space therein. A front part of the inner space of the needle sleeve 1 has a reduced inner diameter. And, an inner peripheral wall 12 of this front part is properly tapered toward a front end of the safety syringe, that is, an end with the cannula C1. A rear part of the inner space of the needle sleeve 1 has an expanded inner diameter relative to the front part, and an inner peripheral wall 13 of the rear part is properly tapered toward the front end of the safety syringe, too. A first shoulder portion 11 is therefore formed between the inner peripheral wall 12 of the front part and the inner peripheral wall 13 of the rear part of the inner space of the needle sleeve 1.

Figure 3:
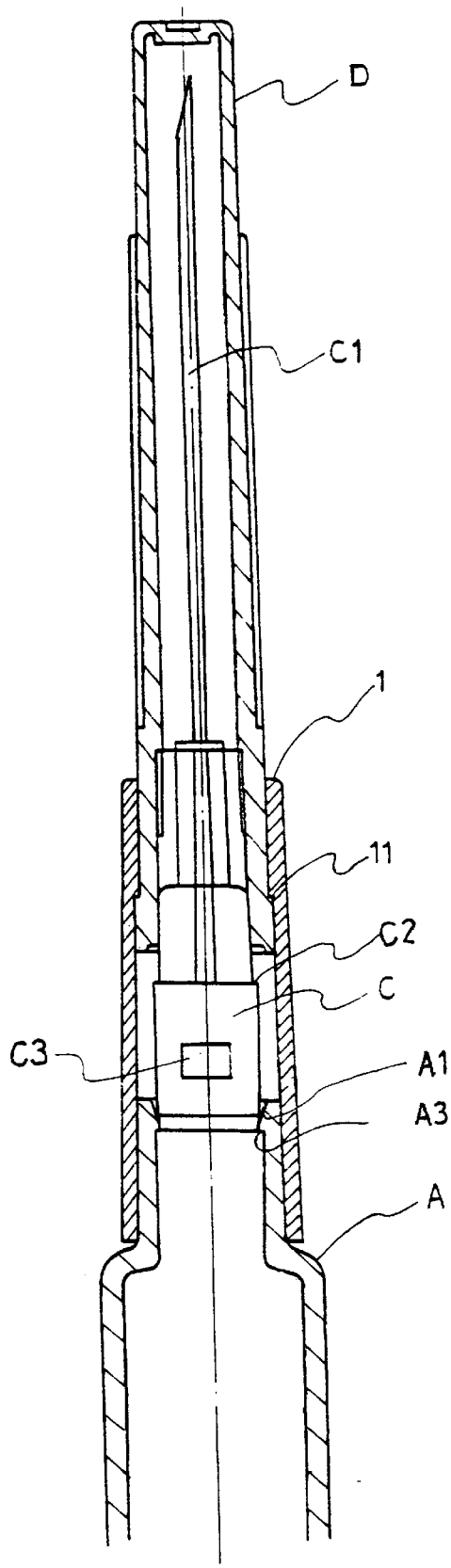
FIG. 3 is an enlarged and fragmentary sectional view of the safety syringe of the present invention showing the manner of assembling the hub, the cap, and the needle sleeve, wherein the hub has not been retained to a neck portion of a barrel of the safety syringe of the present invention.

Please refer to FIGS. 1 and 3. The hub C is formed near a middle portion thereof with a second shoulder portion C2, and at a rear portion thereof with engaging holes C3. The barrel A has a diameter-reduced neck portion A2 that defines a front open end of the barrel A. An inner peripheral wall A1 of the front to open end of the neck portion A2 inclines radially inward. And, a third shoulder portion A3 is formed between the inclined peripheral wall A1 and a straight inner peripheral wall of the neck portion A2 behind the inner open end of the neck portion A2. The cap D includes a slightly forward tapered outer peripheral wall surface D1, and a radially projected flange D2 around a rear bottom of the tapered outer peripheral wall D1.

In assembling the safety syringe of the present invention, first extend the hub C and the cannula C1 connected thereto into the cap D. The cap D is so designated that it has an inner diameter similar to an outer diameter of a portion of the hub C above the second shoulder portion C2, so that the hub C could be tightly fitted in the cap D to form a needle assembly. Thereafter, the needle sleeve 1 is put around the needle assembly from a front end of the cap D, so that the first shoulder portion 11 inside the needle sleeve 1 abuts on the rear flange D2 of the cap D. At this point, a rear end portion of the forward tapered outer peripheral wall surface D1 and the rear flange D2 of the cap D fitly contact with the front and the rear inner peripheral walls 12, 13 of the needle sleeve 1, respectively, with the first shoulder portion 11 abutted against the flange D2. The needle assembly and the needle sleeve 1 put therearound therefore form a needle sleeve assembly. As can be clearly seen from FIG. 3, the hub C is completely covered by the needle sleeve 1 and isolated from external environment and accordingly, any contamination possibly caused by undesirably contacting the cannula. The needle sleeve assembly is then assembled to the barrel A by engaging the inner peripheral wall 13 of the rear part of the needle sleeve 1 with an outer peripheral wall of the reduced neck portion A2 of the barrel A, as shown in FIG. 3, to form a syringe assembly, that is, the safety syringe of the present invention. Before being using to inject a medical liquid, this syringe assembly has a hub C that has a rear bottom portion contacting with the inclined inner peripheral wall A1 at the front open end of the neck portion A2 of the barrel A without being extended into a retained to the neck portion A2. The syringe assembly is then sterilized under high temperature in this state.

Since the hub C is not fully extended into and retained to the neck portion A2 of the barrel A when the syringe assembly is sterilized under high temperature, there would not be any stress produced at this sterilization stage. Therefore, any stress deformation and any thermal deformation of the whole syringe due to such high temperature sterilization could be avoided.

Figure 4:
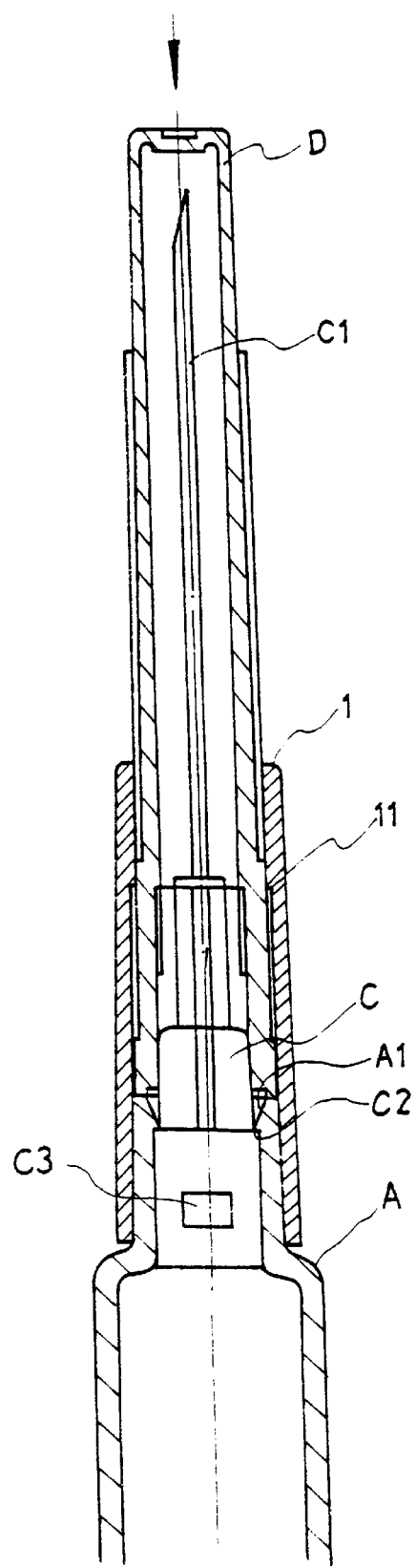
FIG. 4 is a sectional view similar to FIG. 3 but with the hub being retained to the neck portion of the barrel of the safety syringe of the present invention.
Figure 5:
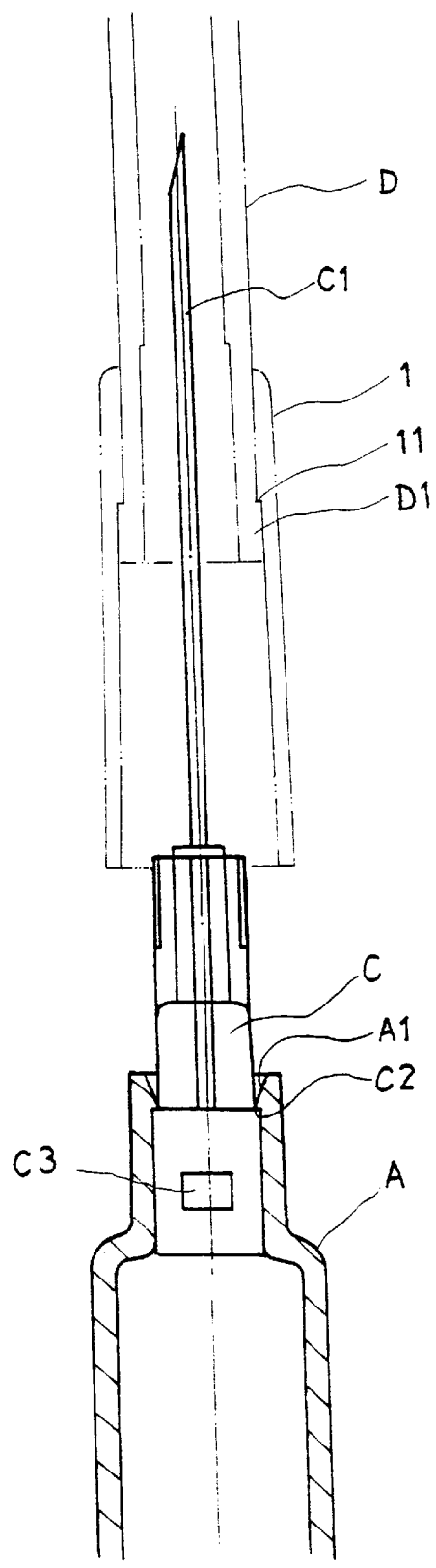
FIG. 5 illustrates the manner of removing the cap and the needle sleeve from the hub and the barrel of the safety syringe of the present invention.

To use the syringe assembly for injection of any medical liquid, a user may depress a front end of the cap D, so that the hub C tightly fitted in the cap D is brought to move downward at the same time. When the second shoulder portion C2 on the hub C is downward moved to pass through the radially inward inclined peripheral wall surface A1 and the third shoulder portion A3 at the front open end of the neck portion A2 of the barrel A, the hub C would not be able to be pulled forward again to separate from the barrel A. At this point, an outer peripheral wall surface of the rear portion of the hub C behind the second shoulder portion C2 would contact with the straight inner peripheral wall surface of the neck portion A2 behind the third shoulder portion A3 in a tight fit relation, as shown in FIG. 4, so that an airtight effect at the joint of the hub C and the barrel A is accomplished. Finally, the cap D is pulled forward to expose the cannula C1. When doing so, the rear bottom flange D2 of the cap D would be moved to abut against the first shoulder portion 11 inside the needle sleeve 1 and therefore brings the needle sleeve 1 to separate from the hub C at the same time, as shown in FIG. 5. After the cap D and the needle sleeve 1 have been removed to expose the cannula C1, the safety syringe of the present invention is ready for use.

Figure 6:
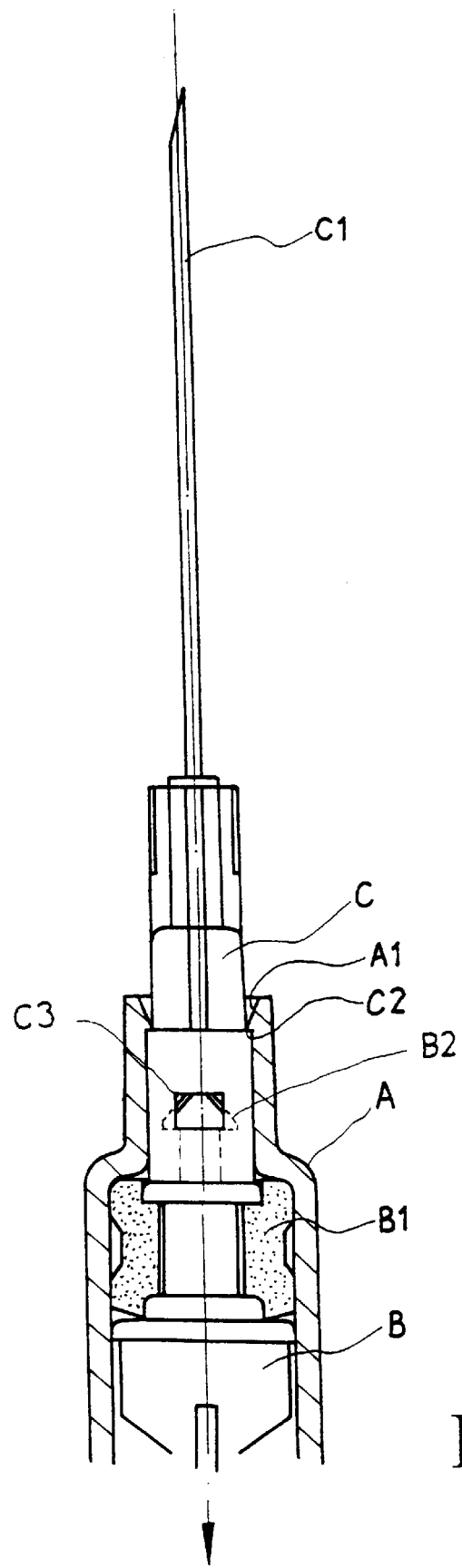
FIG. 6 shows the engagement of a plunger of the safety syringe with the hub when the plunger has been fully pushed forward in the barrel of the safety syringe.
Figure 7:
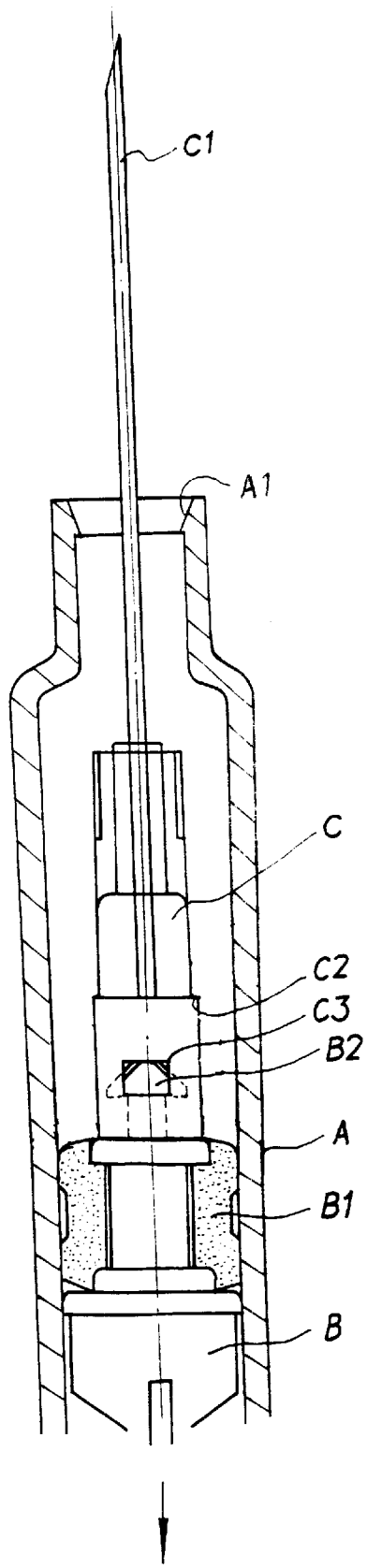
FIG. 7 shows the hub and the cannula are pulled backward by the plunger into the barrel when the cannula has been used.

When using the safety syringe of the present invention to inject a patient with medical liquid, the plunger B is fully pushed forward in the barrel A until an engaging cone B2 provided at a front end of the plunger B engages with the engaging holes C3 provided at the rear portion of the hub C, as shown in FIG. 6. After the injection, the plunger B may be pulled backward to bring the hub C, which is now associated with the plunger B, and the cannula C1, that is connected to the hub C, to move back into the barrel A, as shown in FIG. 7.

The following are some of the advantages of the safety syringe of the present invention.

What is claimed is:

1. A safety syringe apparatus comprising:

a barrel having a tubular front neck portion, said front neck portion having an inner wall inclined radially inward to terminate at a barrel shoulder portion;

a hub having a cannula extending axially therefrom, said hub being coaxially disposed relative to said front neck portion of said barrel for slidably engaged displacement relative thereto between first and second positions, said hub having an axial end portion and a base section extending axially therefrom, said axial end portion abutting said inner wall of said front neck portion in said position, said base section defining an outwardly directed shoulder flange for retentively engaging said barrel shoulder portion in said second position;

a needle sleeve having open lower and upper end portions and an intermediate portion extending therebetween, said lower end portion at least partially ensleeving said barrel front neck portion, said intermediate portion having an inner surface defining a sleeve shoulder portion, said needle sleeve being disposed to extend coaxially about said base section of said hub; and, a cap coupled to said hub for removably covering said cannula, said cap terminating at an open end portion engaging said hub, said cap having formed thereon adjacent said end portion an outwardly directed cap flange, said cap engaging said needle sleeve in slidably displaceable manner through said upper end portion of said needle sleeve;

said cap being axially displaceable relative to said needle sleeve in a first direction to force said hub into said second position, said cap thereafter being axially displaceable relative to said needle sleeve in a second direction for removal from said hub; said cap flange engaging said sleeve shoulder portion to stop said cap displacement relative to said needle sleeve in said second direction, said needle sleeve being thereby locked for removal with said cap from said barrel.

2. The safety syringe apparatus as recited in claim 1 wherein said needle sleeve defines a substantially tubular contour, said inner surface of said needle sleeve being generally tapered in diametric extent, said lower end portion being greater in diametric extend than said upper end portion.

3. The safety syringe apparatus as recited in claim 1 wherein said barrel shoulder and sleeve shoulder portions each define an annular surface directed radially inward.

4. The safety syringe apparatus as recited in claim 3 wherein said shoulder flange and said cap flange each define an annular surface directed radially outward.

* * * * *